United States Patent [19]
Martinell Gisper-Sauch

[11] Patent Number: 6,162,399
[45] Date of Patent: Dec. 19, 2000

[54] UNIVERSAL APPARATUS FOR CLINICAL ANALYSIS

[75] Inventor: Enrique Martinell Gisper-Sauch, Barcelona, Spain

[73] Assignee: Grupo Grifols, S.A., Barcelona, Spain

[21] Appl. No.: 09/121,624

[22] Filed: Jul. 23, 1998

[30] Foreign Application Priority Data

Jul. 30, 1997 [ES] Spain .................................. 9701691

[51] Int. Cl.[7] .................................................. G01N 31/00
[52] U.S. Cl. ............................... 422/64; 422/63; 422/65; 422/72; 422/82.05; 436/43; 436/45; 436/47; 436/48; 436/164; 436/174; 436/180
[58] Field of Search .............................. 422/63, 64, 65, 422/72, 82.05; 436/43, 45, 47, 48, 164, 174, 180

[56] References Cited

U.S. PATENT DOCUMENTS

| | | | |
|---|---|---|---|
| 5,122,342 | 6/1992 | McCulloch et al. ...................... | 422/65 |
| 5,232,665 | 8/1993 | Burkovich et al. ...................... | 422/65 |
| 5,374,395 | 12/1994 | Robinson et al. ...................... | 422/64 |
| 5,424,036 | 6/1995 | Ushikubo ................................. | 422/64 |
| 5,578,269 | 11/1996 | Yaremko et al. ......................... | 422/64 |
| 5,580,524 | 12/1996 | Forrest et al. ............................ | 422/63 |
| 5,681,530 | 10/1997 | Kuster et al. ............................. | 422/63 |
| 5,762,873 | 6/1998 | Fanning et al. .......................... | 422/65 |
| 5,779,985 | 7/1998 | Sucholeiki .............................. | 422/128 |
| 5,814,277 | 9/1998 | Bell et al. ................................. | 422/67 |

*Primary Examiner*—Jill Warden
*Assistant Examiner*—Kath Bex
*Attorney, Agent, or Firm*—Darby & Darby

[57] ABSTRACT

A universal apparatus for clinical analysis is provided comprising a base-board having three main levels. The first level holds a terminal for containers of reagents and samples and includes a device for cyclically vibrating individual vials. External graphic marks on vials and bottles and the internal characteristics of the same, such as the level of contents can be read. The second level of the base-board includes a thermostatic block which is provided with a number of grooves which can receive either disposable strips of small analytical containers or analytical cards. An agglutination reader is also provided. The third level carries a centrifuge which receives either strips or cards from a collection head having a clamp for collecting, conveying and placing in position the strips and cards; the head also including a pipetting needle.

9 Claims, 12 Drawing Sheets

UNIVERSAL APPARATUS FOR CLINICAL ANALYSIS

DESCRIPTION

The present invention relates to an apparatus for clinical analysis by means of which it is possible to carry out clinical analysis of samples completely in an automated manner, providing characteristics of novelty and inventive activity as compared with analytical equipment known at the present time.

One aim of the present invention is to provide a universal analytical apparatus in which in a complete and very simplified manner it is possible to carry out automatically all stages of receiving samples, preparing the same, including subjecting them to centrifugation, culturing and assessing the analytical results, the components of this apparatus being arranged in a very straightforward manner and the external dimensions of the apparatus being on a small scale, enabling the apparatus to be used both for cards carrying reagents for analysis and for strips of pockets or small containers designed to receive the samples and reagents themselves.

Another aim of the present invention is to provide an apparatus with a double terminal carrying reagents and samples, which is provided with a system for supporting and individually stirring each of the reagent vials, as well as a support for the diluent bottles, this terminal being combined with a terminal for reading the inscriptions of a bar code or other marks, this terminal being provided in an open peripheral area in a surrounding alignment of test tubes which is arranged in the external part of the terminal.

Also, it is an aim of the present invention to provide an analytical apparatus in which there is provided a single collection head carrying a fastening clamp which can be used both for tubes for small reaction containers and for cards and which also carries a system for pipetting by means of a directly perforating needle in order to handle liquids, in particular the reagents.

Another aim of the present invention is to provide an analytical universal apparatus for analysing samples, which is provided with a universal head for making readings of agglutinations, appropriate both for reading cards and also for reading strips of small containers or pockets for holding the samples, the apparatus also having a built-in orbital stirring system.

Still another aim of the apparatus which is the subject of the present invention, it is to provide blocks or areas of support which can be used indiscriminately in connection with strips of pockets and/or cards which are used alongside these, for culturing at the control temperature and for the resting and waiting area, using a system for retaining the cards in order to prevent them from being removed by the pipetting needle as it withdraws after it has pierced the cover of the card.

In order to achieve its aims, the apparatus of the present invention provides, on a staggered base-board, a lateral area which is completely occupied by the unit holding the vials for reagents and the alignment of test tubes for samples, as well as the reading unit which is incorporated into an opening in the test tube alignment. In the highest part of the staggered board there are provided areas for receiving the strips of small containers or cards which are intended to enable the different contiguous areas of rest, culturing and assessment of results, to be separated from each other while the apparatus presents at the extremity opposite the unit holding the vials of reagents and the alignment of test tubes, a single head which has a universal clamp designed to fasten both strips of pockets for samples and also cards for reagents, this head also holding the pipetting needle and its driving members, a system of guides being provided for the purpose of movement relatively to the axes X-Y of the base-board of the apparatus and to the axis Z of the head itself, in order both to enable the head and the collection clamp to move over the board of the apparatus and to enable the pipetting needle to rise and fall.

The centrifuge is incorporated in the side of the apparatus opposite the unit holding the vials of reagents and test tubes at a somewhat lower level than the tube supports, the latter being accessible only through a fixed window of the cover designed to hold the clamp for collecting or depositing the units of sample cubes or analytical plates.

In order to facilitate the understanding of this invention, various drawings are attached showing one form of universal analytical apparatus which has been constructed according to the present invention, by way of non-restrictive representative example.

Figure 1:
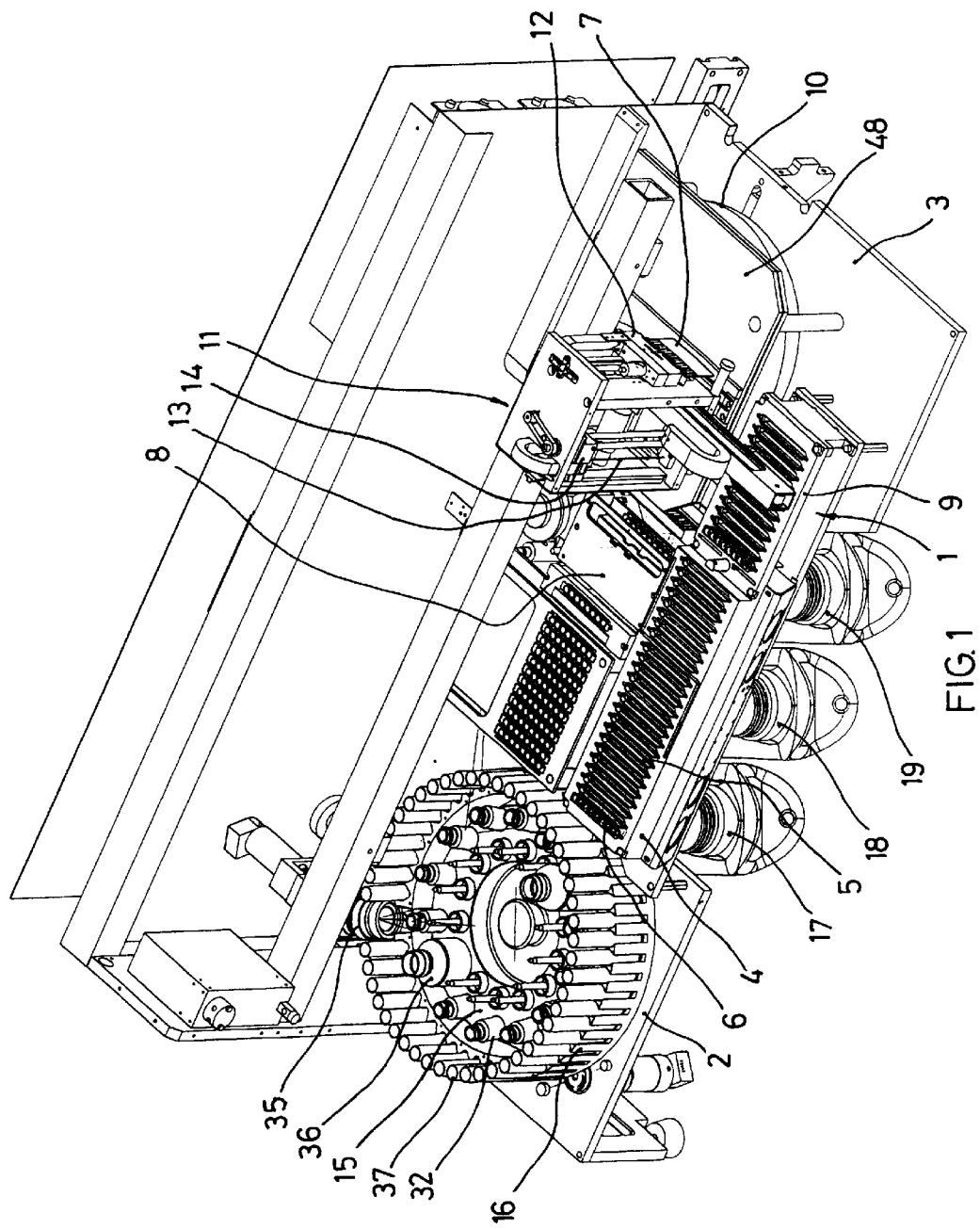
FIG. 1 shows a simplified perspective view of an apparatus according to the present invention.
Figure 2:
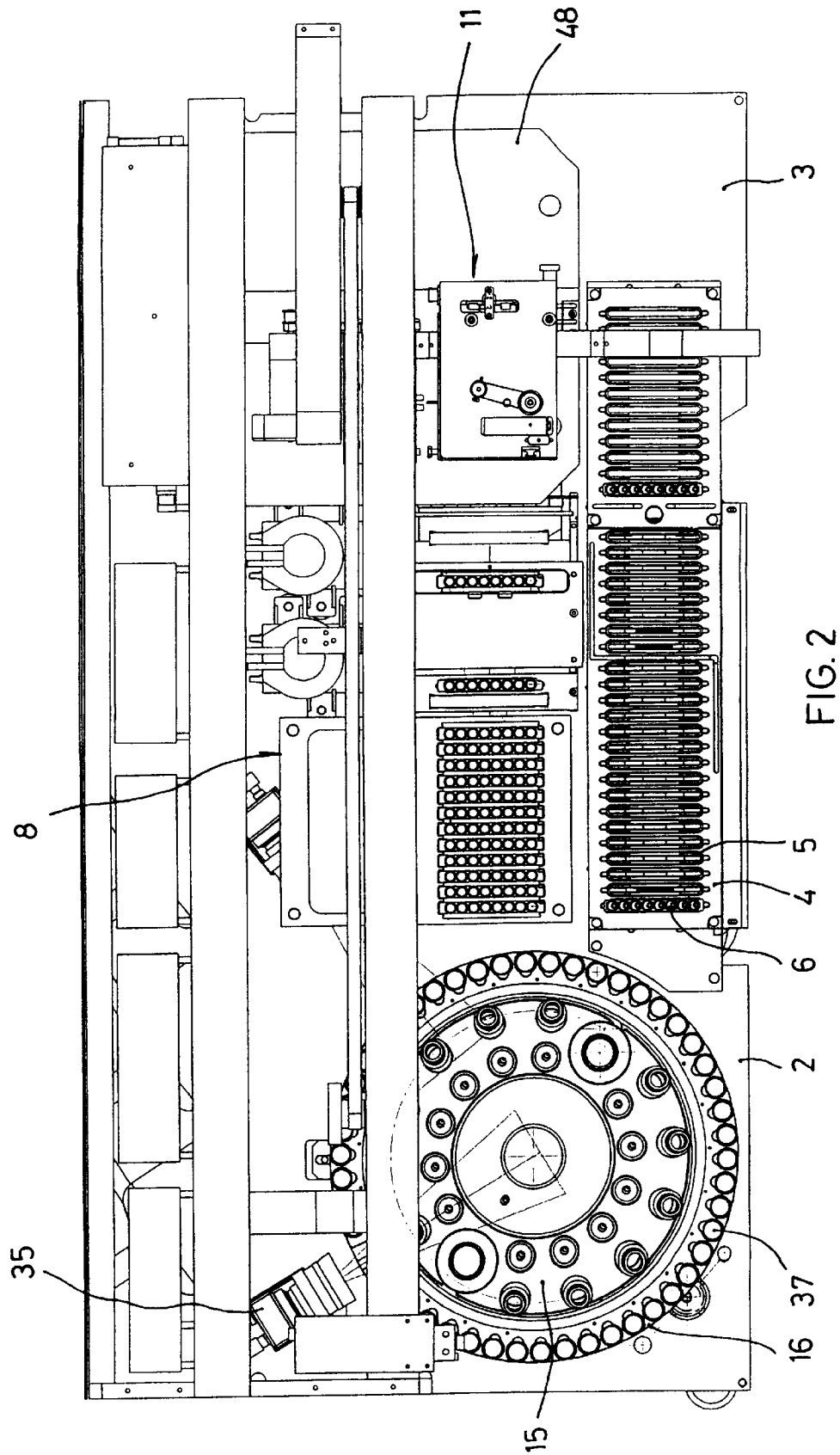
FIG. 2 shows a plan view of the apparatus of FIG. 1.
Figure 3:
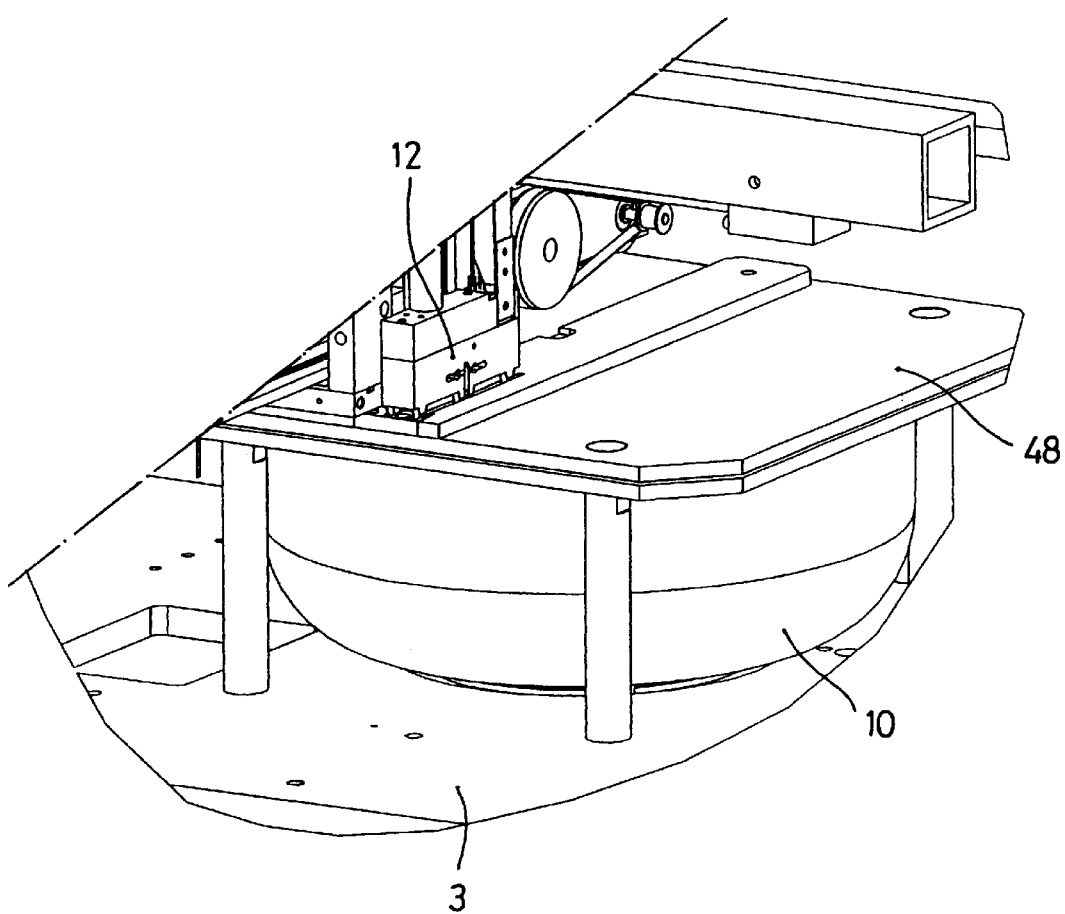
FIG. 3 shows a view in perspective of an area of the apparatus corresponding to the position of the collection clamp and the centrifuge.
Figure 7:
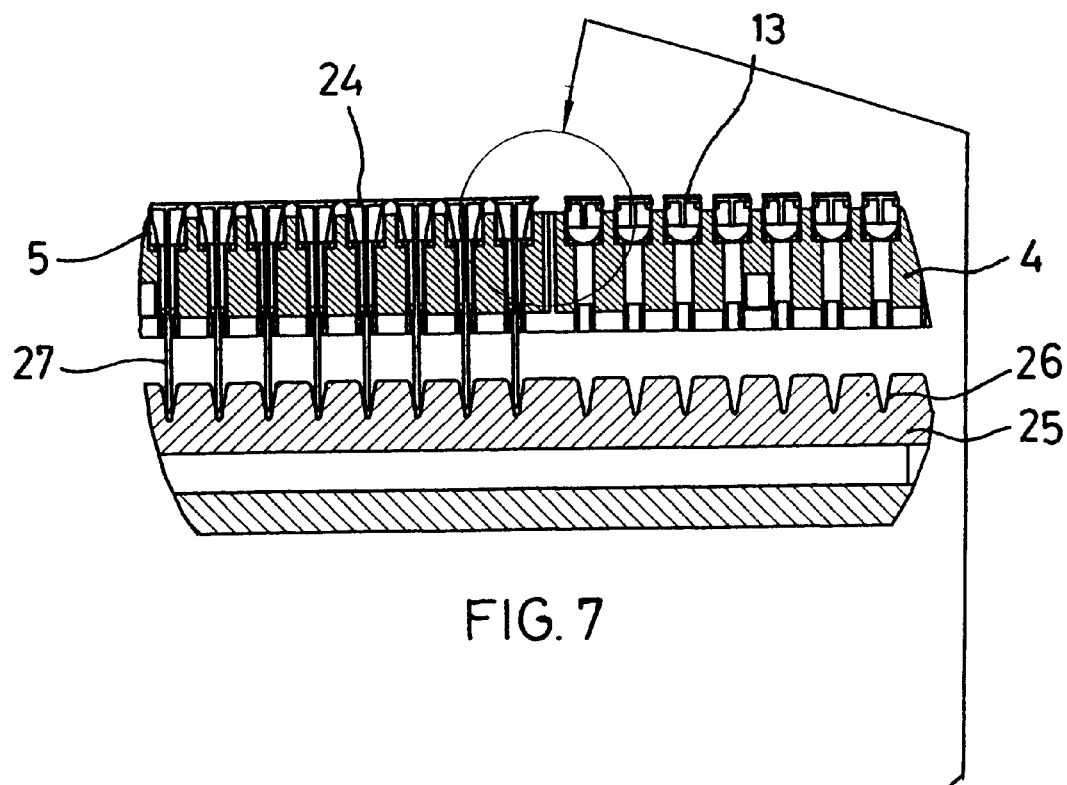
FIG. 7 is a detailed view of a section of a zone for depositing and retaining alignment of the analytical trays and plates.

As can be seen in FIG. 1, the analytical apparatus provided by the present invention comprises a base-board with various levels, designed in order to improve the automatic handling features of the apparatus, and to reduce the dimensions and comprising a central area 1 and two peripheral areas 2 and 3 at lower levels, the first area being designed to hold the thermostatic block 4 which is provided with a number of housing grooves 5, the said grooves being designed to receive either a strip 6 of small containers of disposable reagents or an analytical card, as shown diagrammatically by the FIG. 7. In the central area 1 itself the universal reader 8 for binding agents is arranged together with a resting area or block 9 in which doubtful cases can be lodged. On the third level 3 the centrifuge 10 is installed, having an upper cover 48 creating another level upon which the head 11 is movably mounted, the said head holding the clamp 12 for fastening and conveying the plates and the disposable strips, the head also holding a pipetting system which is provided with a piercing needle 13. The said head 11 moves over coordinated axes of the apparatus frame and within itself comprises guides for a second pair of coordinated axes so that both the clamp 12 and also the pipetting needle 13 with its control unit 14 can move optionally.

On level 2, the apparatus is provided with the reagent terminal 15 and with a carousel 16 for samples.

The liquids, such as diluents and others, are fed through bottles 17, 18 and 19, which can vary in number, the said bottles being arranged below the intermediate area 1 of the board.

Figure 4:
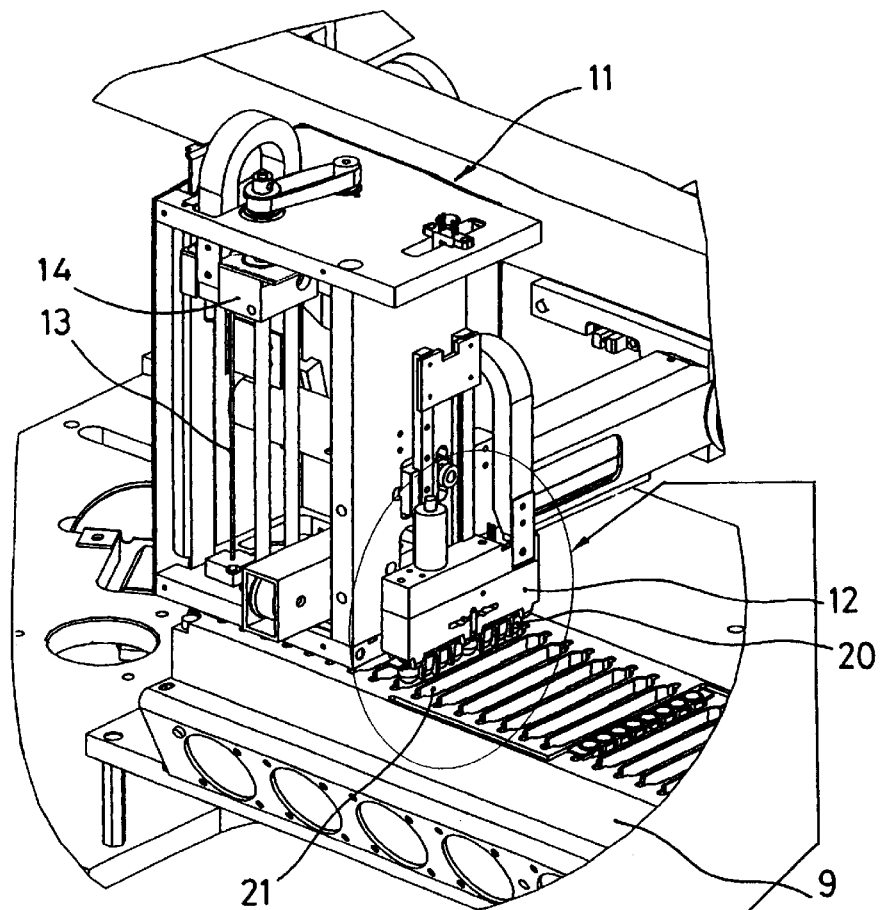
FIGS. 4 and 5 are separate views in simple perspective of the collection head and a detail of the clamp, respectively.
Figure 5:
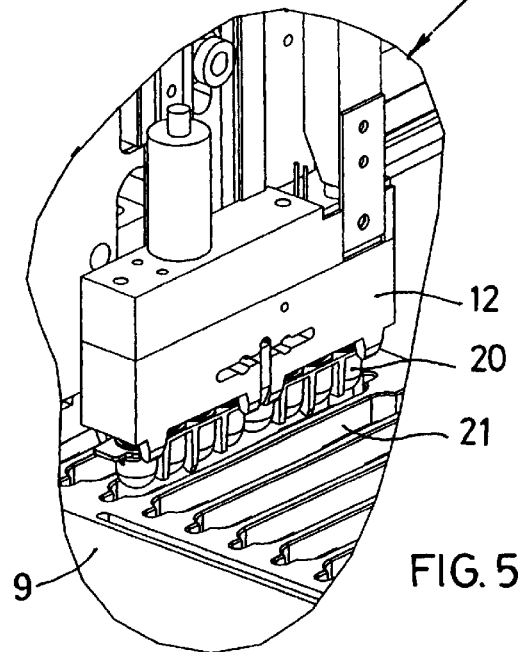

As has been shown in the drawings, one of the main characteristics of the apparatus shown is that it can be used indiscriminately for the handling of disposable strips of pockets, or analytical cards. In FIGS. 4 and 5 the conveyance head 11 can be seen situated above the block 9 which receives the strips and the cards, so that the clamp 12 is arranged, by way of an example, in the lower part of its vertical movement path, as it collects a disposable strip 20 of analytical pockets. In FIG. 5 the relative position of the clamp can be seen, in relation to one of the pockets 21 which are designed to receive the separable strips and the analytical cards.

Figure 6:
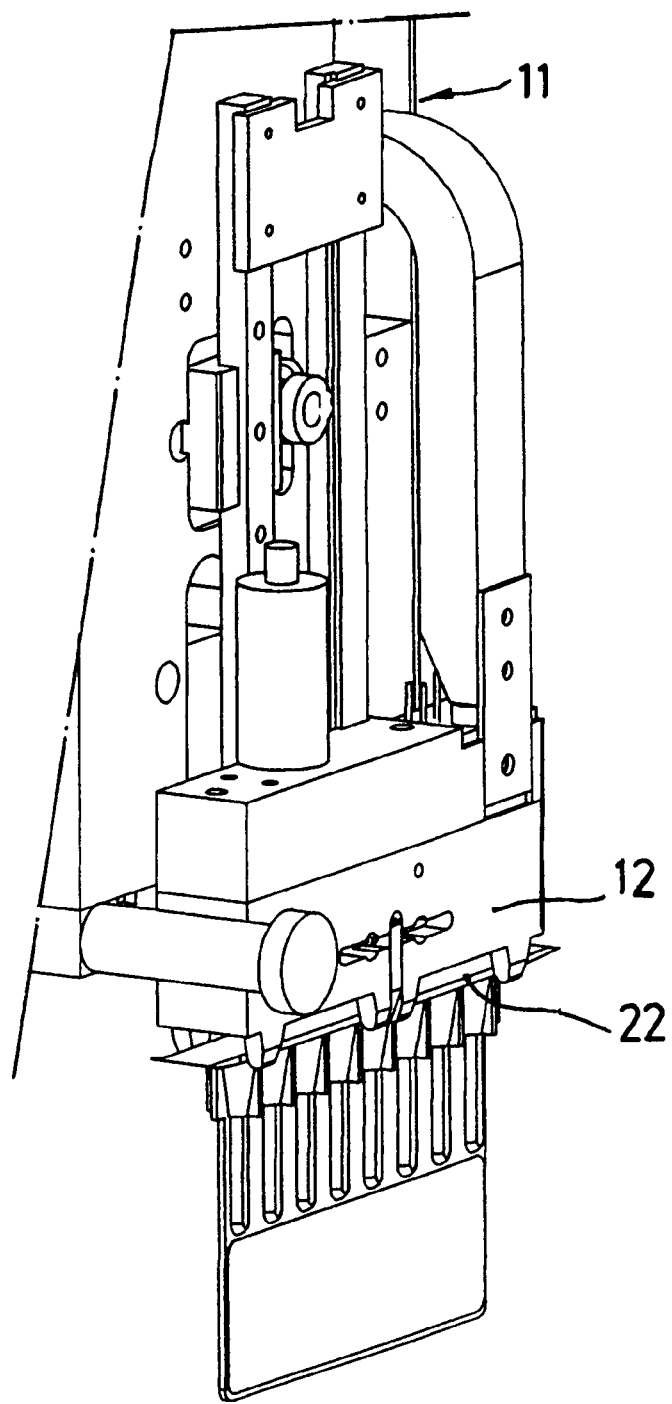
FIG. 6 shows on a larger scale a detail of the clamp for handling the strips and cards of reagents.

In FIG. 6 the clamp itself 12 can be seen, picking up an analytical plate 22.

In order to obtain the dual function referred to, it must be understood that both the clamp and the receiving pockets in the various blocks of the apparatus must be capable of receiving indiscriminately any of the two above-mentioned components, i.e. a disposable strip of small analytical containers or a card.

Figure 8:
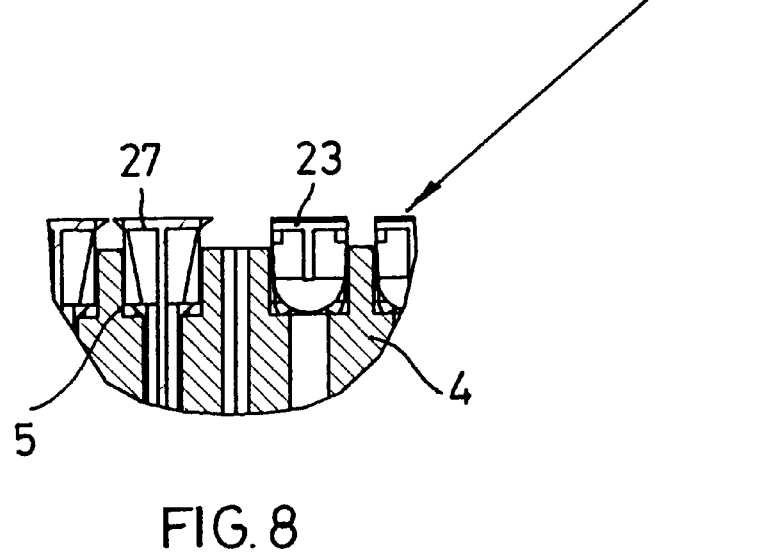
FIG. 8 is an enlarged view of the designated portion of FIG. 7.

As can be seen in FIGS. 7 and 8, block 4 contains various grooves 5 which are capable of receiving indiscriminately either strips of the disposable type 23 or cards 24. In the case of the cards 24, in order to prevent the card from being extracted by the pipetting needle in its withdrawal movement, the apparatus is designed to include a lower block 25 which is provided with a number of grooves 26 the cross-section of which is in the form of a very tight acute-angled V shape, in order to hold the lower edge 27 of each of the cards 24. Thus the card is slightly wedged inside the corresponding groove, preventing it from being removed unnecessarily from the said groove.

Figure 9:
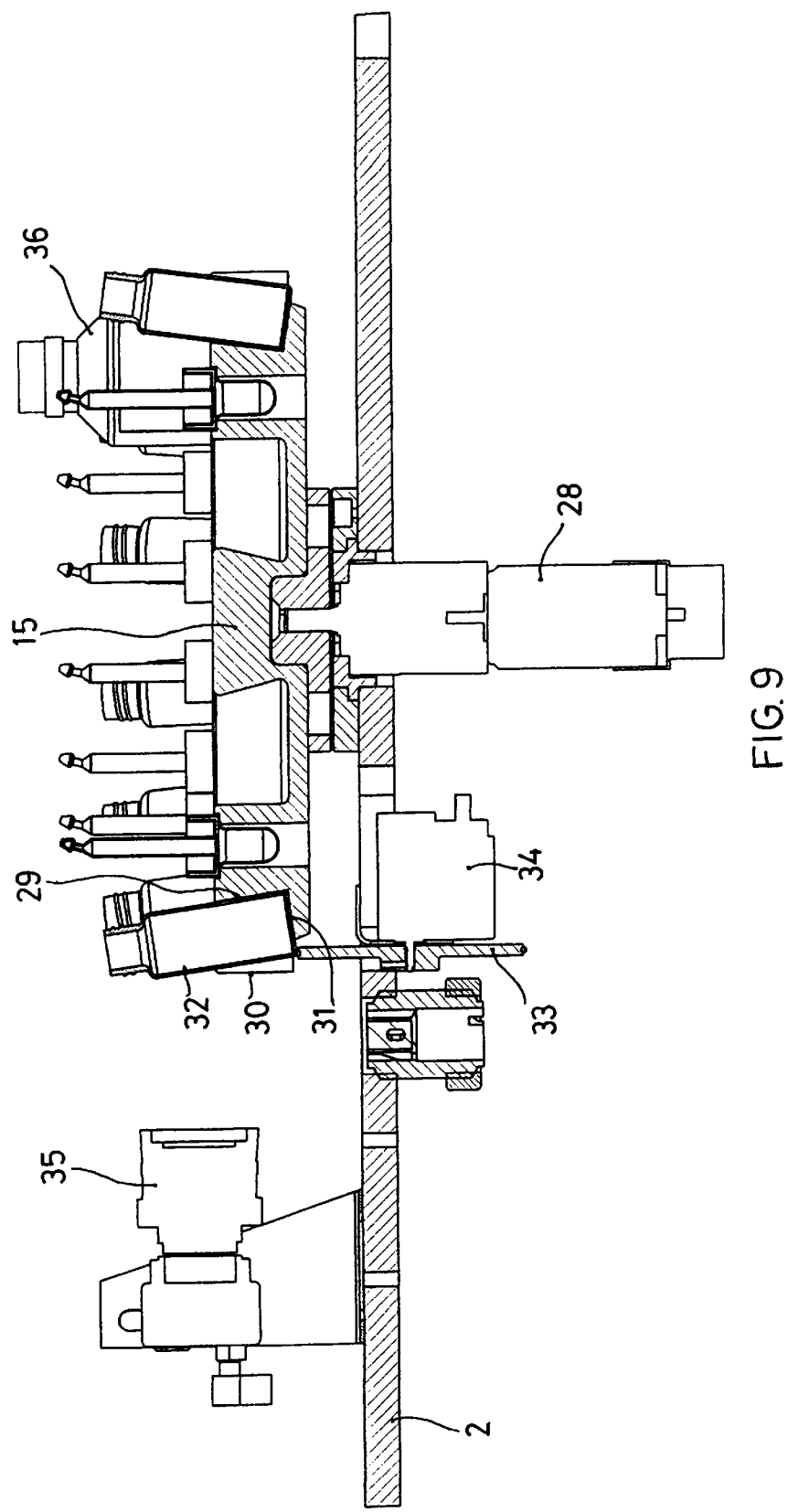
FIG. 9 shows a simplified section of the unit holding vials and bottles of reagents.
Figure 10:
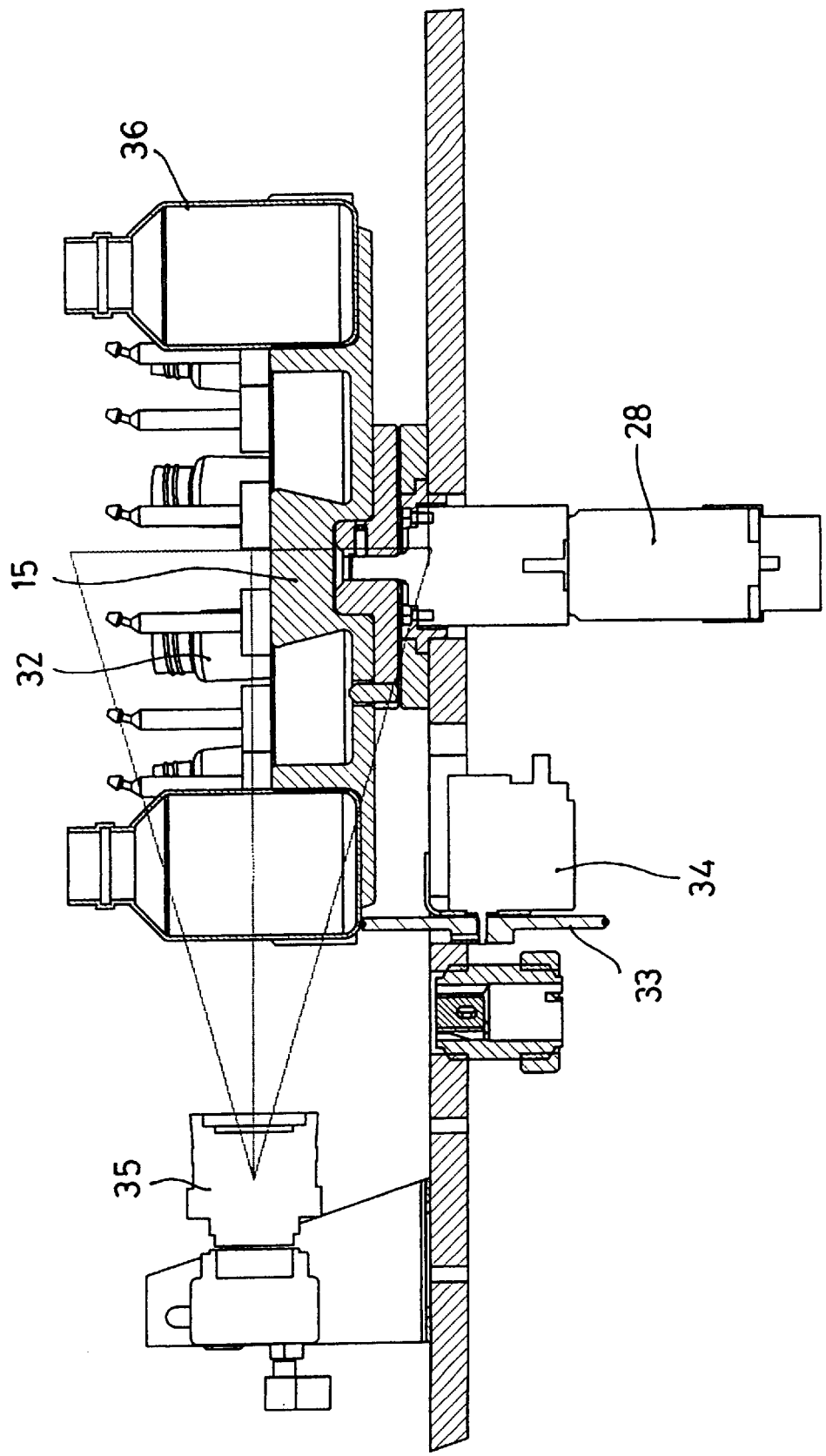
FIG. 10 shows a section which is similar to FIG. 9 indicating the arrangement of bottles of reagents.

The reagent and samples terminal 15 has been shown in greater detail in FIGS. 9 and 10, showing that its construction includes a central plate which revolves on its symmetrical axis by means of a lower driving unit 28, which is provided with a number of peripheral openings 29 which are arranged in a sloping manner in an outward direction, so that the axes of the said openings or housings create an acute angle with the geometrical turning axis of the plate 15. Simultaneously, the external part 30 of the said housings 29 is free, i.e. open, exposing a portion of the base 31 of the containers for reagents 32. This arrangement enables each of the said containers 32 to be turned periodically by means of the provision of a rotating disc 33 below the plate for the reagent unit, the said disc being turned by the reducing motor 34 and making contact through its periphery at a point adjoining the edge of the base or floor 31 of the container 32, as has been shown FIG. 9. In this way, each time that the plate holding reagents passes in its gyratory path through the position corresponding to the disc 33, the corresponding container or vial is turned over the cavity 29, which enables the reagents to be stirred effectively.

The vials or containers of reagents will be agitated at a variable speed, since the driving unit 34 comprises a motor with a speed reducer.

By means of this arrangement it will be possible for the vials of reagents to be aligned automatically so that it is possible to read by means of the CCD device, the bar code, the level of reagent, the size of the vial and the quality of the stirring process, all of which is carried out by means of the CCD camera 35 which is mounted on level 2 of the apparatus. Moreover, this arrangement makes it possible for the diluent bottles 36 to be automatically aligned in order to facilitate reading of the bar code, the level of diluent, the size of the bottle and other data, by means of the CCD, as can be seen in greater detail in FIG. 10. The capacity to stir the red cells at different speeds is also obtained.

The vials and containers of diluents are read at a common point by means of the same CCD 35, which has the capacity to read the reagents through a window of the sample-holding carousel 16, holding the various test tubes 37, as can be seen in FIG. 1. In order to facilitate reading by the CCD, a double lighting system has been incorporated for the purpose of enabling the bar code to be read with the aid of a front lighting system for the purpose of determining the quality of the stirring process and the size of the vial/bottle as well as a rear lighting system for determining the level of liquid which remains in each vial/bottle.

As previously described, the mobile head 11 is designed both for the purpose of placing the pipetting system in suitable areas of the board and of conveying the cards or strips to the appropriate position. In this way, the dispensing needle 13 can move in order to reach the carousels, the dilution terminal and the blocks. The clamp 12 can reach the blocks, the stirring unit, the reader and the centrifuge.

Figure 11:
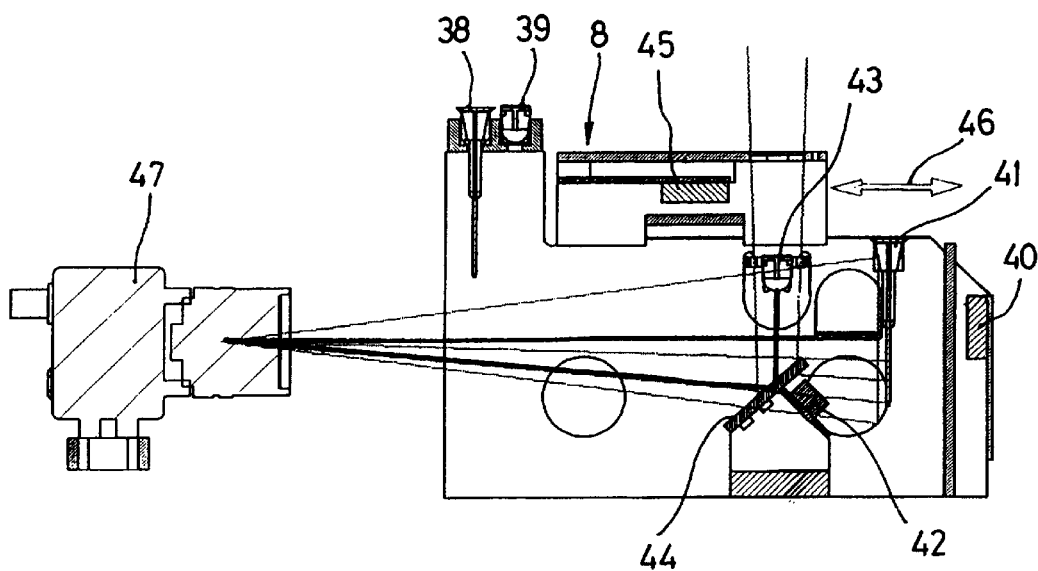
FIG. 11 is a simplified section of the reading head for analysis, which is suitable both for strips of pockets holding samples and for analytical cards.
Figure 12:
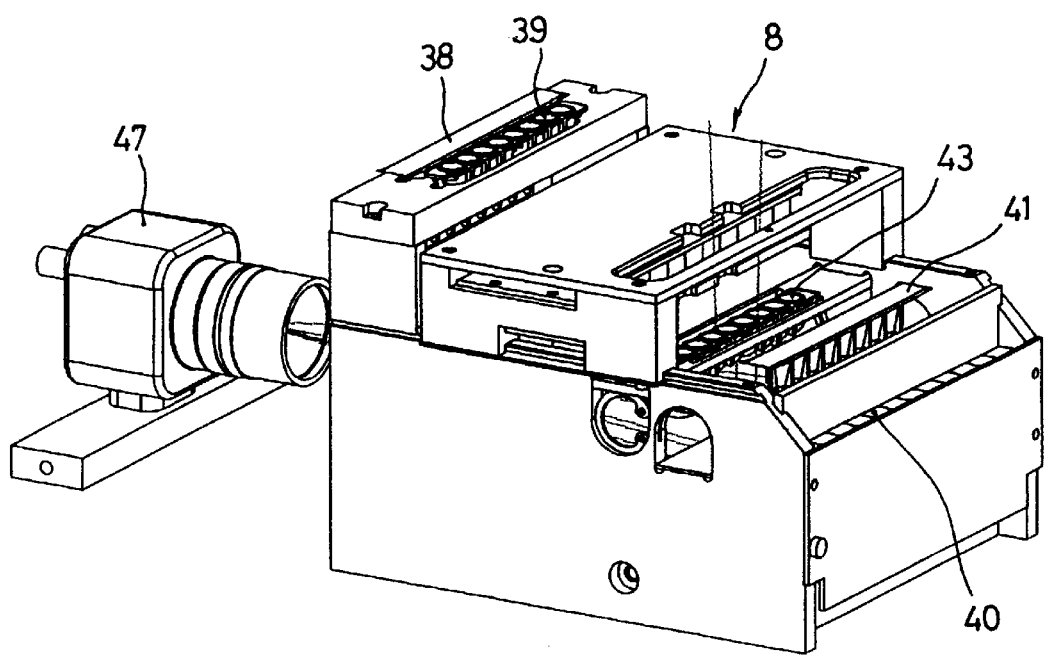
FIG. 12 shows a view in perspective of the unit in FIG. 11.
Figure 13:
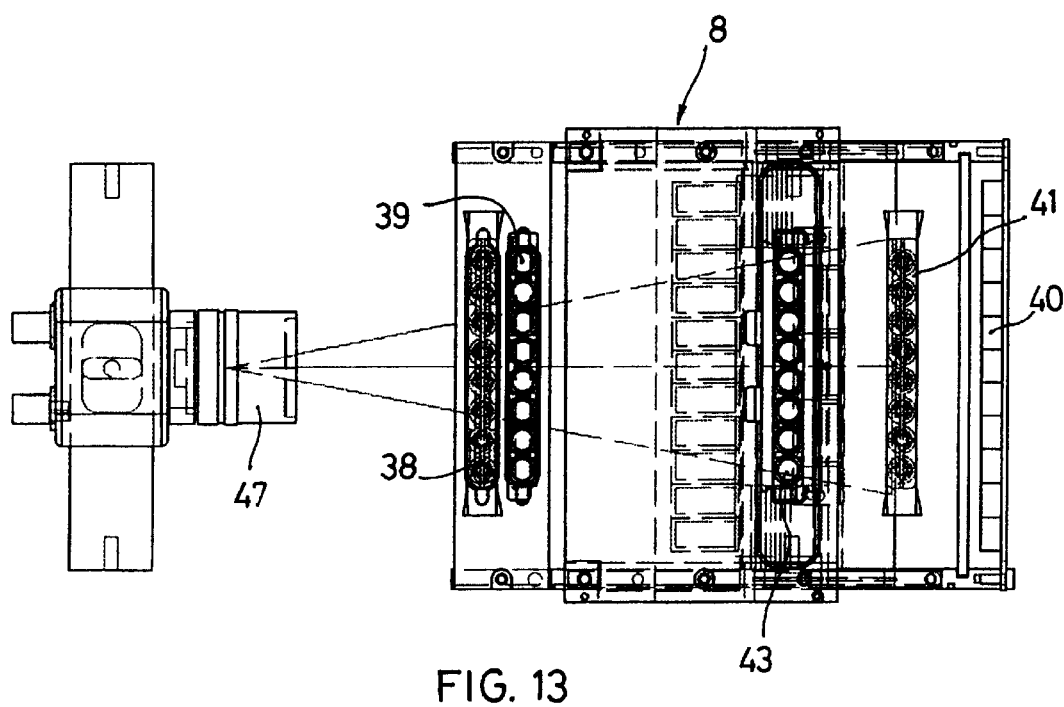
FIG. 13 is a plan view showing the position of the camera which is provided for photographing the strips of pockets or the analytical cards for assessing the result of the analysis.

The universal reader of agglutinations shown in FIGS. 11, 12 and 13 is designed to read indiscriminately both cards and strips, as shown respectively by reference numerals 38 and 39 in FIG. 11 and this reader is based upon a single CCD reader 38 and two separate reading systems with an independent lighting system. In the case of reading a card 41, the latter is placed in a reading position and is targeted by the conveyance system itself while the photograph is being taken. The small containers are lit from the rear by means of a system of LEDs and a diffuser 40. A second lighting system 42 in the front enables the bar code to be read.

A disposable strip 43 can be read after lodging the strip on a suitable base and reading the strip from the base by way of a mirror 44 which is suitably tilted. The lighting system 45 which is movable in the direction indicated by the arrow 46 is located in relation to the upper part of the strip by means of the conveyance system.

The strips are shaken in an identical orbital manner at all points on the surface, the shaking mechanism being housed in a stand connected to an eccentric wheel which turns in rigid relationship with the axis of the motor. The stand is also supported by means of its ends which are resiliently mounted on the base.

Figure 14:
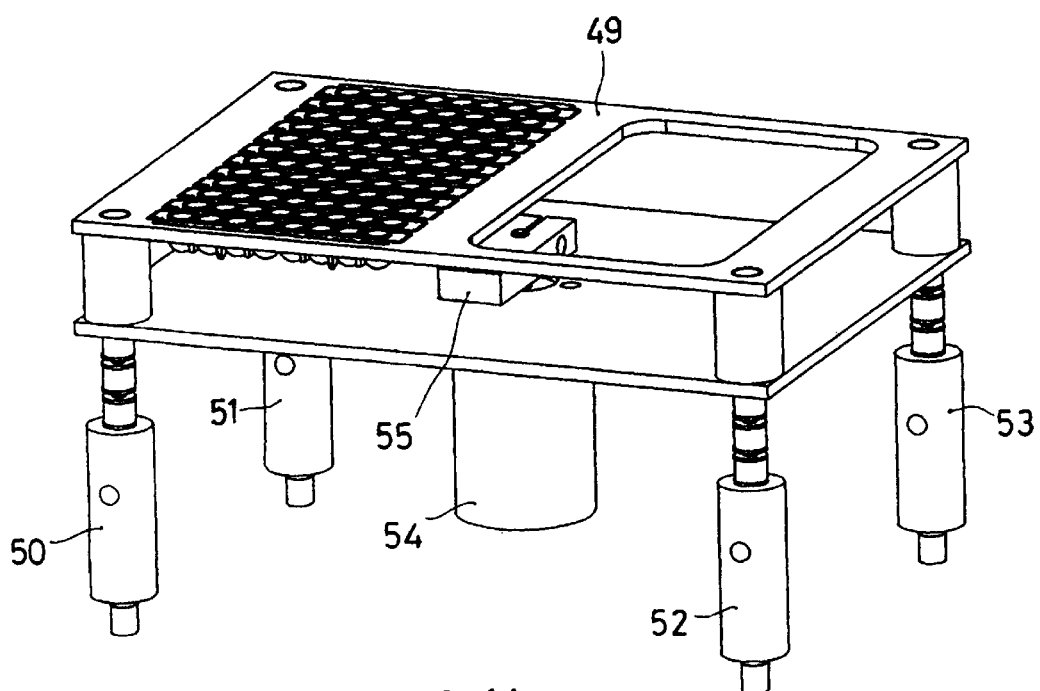
FIG. 14 shows a view in perspective of the support unit for orbital stirring of the samples.

The orbital stirring unit is shown in FIG. 14, in which there can be seen the holding board 49 the said board being provided with four supporting feet 50, 51, 52 and 53 which incorporate elastic blocks of the kind commonly known by the name "silentbloc" constructed in such a manner that orbital oscillation can be produced in the board 49 by rotation of the motor 54 which is housed in the lower part of the board itself and which is connected to a radially mounted eccentric mass 55.

As can be understood, using the combined means which have been described above, it is possible in a single apparatus to process gel cards and disposable strips since all the components required can receive and handle either one or the other. Also it is possible to identify positively the reagents, diluents and samples and to track non-intrusively the level of washing and waste solutions based on load cells. Also this apparatus makes it possible to identify positively the cards and strips and to undertake quality control of the supports by verifying the gel level, etc. In addition it makes it possible to carry out pipetting of the samples and reagents rationally in the heating blocks and also to provide an intelligent type of level detector, coagulation detectors, digital pump, etc.

Also, the fact that the board for the apparatus is constructed on various levels and the precise arrangement of its integral units are aimed at facilitating the various handling processes and in particular at reducing the sweep of the mobile head and that of the fastening and conveying clamp.

This structure will also enable the apparatus which is the subject of the present invention to convey both strips and cards and to carry out readings based on a single CCD device for the two stands of strips and cards.

What is claimed is:

1. Universal apparatus for clinical analysis including preparing, handling and analyzing clinical samples, comprising a base-board having a first, second and a third level respectively spaced from each other, said first level having a terminal for receiving containers having reagents or samples therein, said terminal including agitation means for cyclical agitation of individual containers received therein, and reading means for reading external graphic markings on the containers and the internal characteristics of the materials in the containers; said second level having a built-in thermostatic block provided with a plurality of grooves sized to receive either disposable strips comprising small analytical containers or analytical cards, a universal reader for agglutinations, and an orbital stirring device for stirring either the cards or the strips; said third level having a centrifuge having receiving means sized to receive either strips or cards; and a bead having a single clamp for collecting, conveying and placing in position either a strip or card, said clamp including a pipetting system having a needle, and mounting means for mounting said head oil said base-board for movement relative to said base-board about two coordinated axes, and a third axes so as to move said needle with respect to said base-board.

2. Universal apparatus for clinical analysis according to claim 1, characterized in that the reagent terminal comprises a central rotatable plate, a motor for rotating said central plate, a plurality of cylindrical cavities at the periphery of said plate adapted to receive containers therein, the respective axes of each one of said plurality of cavities being tilted relative to the axes of said plate, each of said plurality of cavities having an opening to expose a portion of the container received therein to permit viewing of the contents of the container, said agitation means comprising a second motor, and a disc connected to said second motor and positioned to engage the container received in the cavity as said plate rotates, to rotate the containers and cause agitation of the contents thereof.

3. Universal apparatus for clinical analysis according to claim 2, characterized in that said plate is provided with a plurality of housings for bottles of diluent, said plurality of housings being concentrically arranged with respect to said plurality of cavities, the axes of respective ones of said housings being parallel to the axis of rotation of said plate.

4. Universal apparatus for clinical analysis according to claim 2, characterized in that a fixed external carousel is arranged on said plate, said carousel being positioned concentrically in relation to the plate, and test tube supports on said carousel, said carousel having an opening for receiving a CCD device to provide a single reading of the materials received in the containers.

5. Universal apparatus for clinical analysis according to claim 4, characterized in that a first and a second lighting system are provided which are connected with said terminal, said first lighting system being mounted on said base-board and positioned to illuminate bar codes on the containers for the reagents to permit a CCD device to read said bar code, said second lighting system being positioned to facilitate reading of the levels and the parameters of the contents thereof.

6. Universal apparatus for clinical analysis according to claim 4, characterized in that a second non-thermostatic block is positioned under said thermostatic block, said second block being provided with respective grooves in alignment with respective ones of the plurality of grooves in said thermostatic block, and having a cross-section in the form of an acute-angled V, whereby said grooves in said second block retain the lower edge of each of the cards received in said first block to prevent the same from being removed from the thermostatic block groove when said pipetting needle is removed from a card.

7. Universal apparatus for clinical analysis according to claim 1, characterized in that said universal reader includes a rear lighting system comprising LEDs and a diffuser, and a second front lighting system for illuminating bar codes on the containers.

8. Universal apparatus for clinical analysis according to claim 7, characterized in that said reader includes a light source mounted on said head and movable therewith, and a tilted mirror provided in the path of the light beam from said light source to reflect said beam onto the container to be read.

9. Universal apparatus for clinical analysis as in claim 1, in which said apparatus includes a frame, and said orbital stirring device comprises a motor mounted on said base-board and having an eccentric mass attached thereto, a board for receiving either card or strip containers connected to said motor and adapted to be vibrated thereby, and a plurality of resilient supports connecting said board to said frame.

* * * * *